US00PP18544P3

(12) United States Plant Patent
Boeder

(10) Patent No.: US PP18,544 P3
(45) Date of Patent: Mar. 4, 2008

(54) ***CHRYSANTHEMUM* PLANT NAMED LIBRA**

(50) Latin Name: *Chrysanthemum morifolium*
Varietal Denomination: Libra

(75) Inventor: Mark Roland Boeder, The Hague (NL)

(73) Assignee: Chrysanthemum Breeders Association N.V., Aalsmeer (NL)

( * ) Notice: Subject to any disclaimer, the term of this patent is extended or adjusted under 35 U.S.C. 154(b) by 0 days.

(21) Appl. No.: 11/304,553

(22) Filed: Dec. 16, 2005

(65) Prior Publication Data

US 2007/0143902 P1 Jun. 21, 2007

(51) Int. Cl.
*A01H 5/00* (2006.01)

(52) U.S. Cl. ..... Plt./287

(58) Field of Classification Search ..... Plt./287
See application file for complete search history.

(56) References Cited

U.S. PATENT DOCUMENTS

2007/0143902 P1 * 6/2007 Boeder ..... Plt./286

* cited by examiner

*Primary Examiner*—Wendy C. Haas
*Assistant Examiner*—Georgia Helmer
(74) *Attorney, Agent, or Firm*—Steptoe & Johnson LLP

(57) ABSTRACT

A *chrysanthemum* plant named Libra characterized by its medium sized blooms with white ray florets and a cream center, and prolife branching; natural season flower date August 29–September 4; blooming for a period of 5 weeks.

3 Drawing Sheets

BACKGROUND OF THE INVENTION

Libra is a product of a breeding and selection program for outdoor pot mums (garden mums) which had the objective of creating new *chrysanthemum* cultivars with a decorative type flower, a natural season flower date around August 29–September 4; blooming for a period of 5 weeks. The new plant of the present invention comprises a new and distinct cultivar of *chrysanthemum* plant. Libra is a seedling resulting from a crossing program, set up by a previous breeder, and which records are unknown to the inventor. The new and distinct cultivar was discovered and selected as a flowering plant by Mark Roland Boeder on a cultivated field in Rijsenhout, The Netherlands in 2001. The first act of asexual production of Libra was accomplished when vegetative cuttings were taken from the initial selection in 2001 and propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

Figure 1:
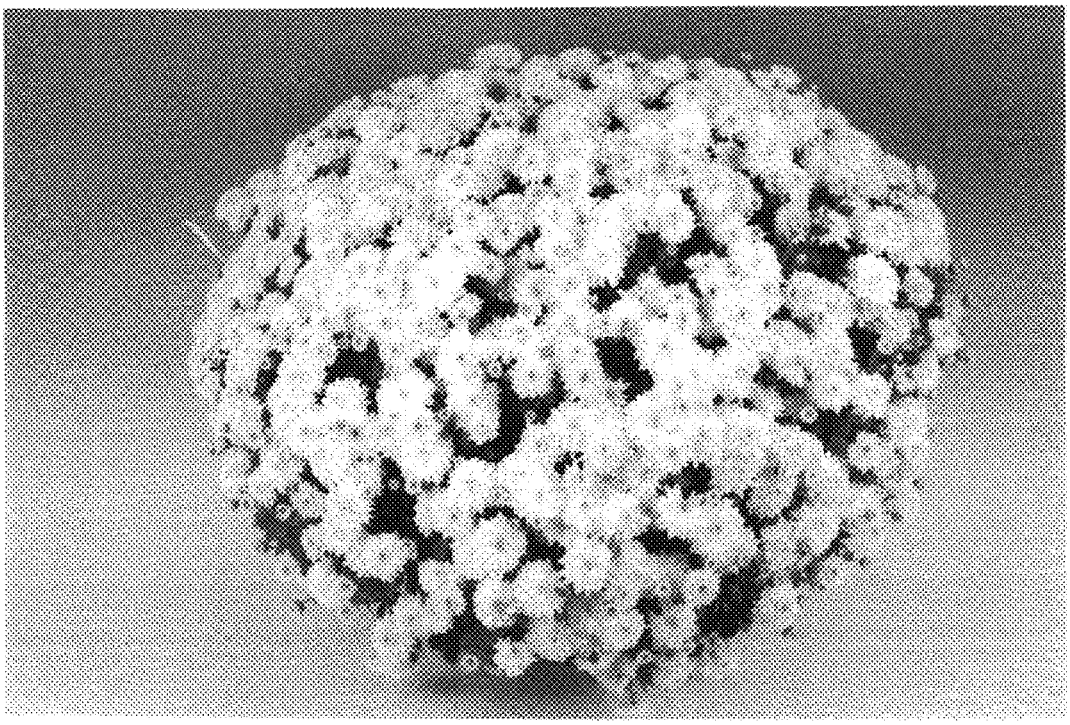
FIG. 1 shows a plant of the cultivar in full bloom.
Figure 2:
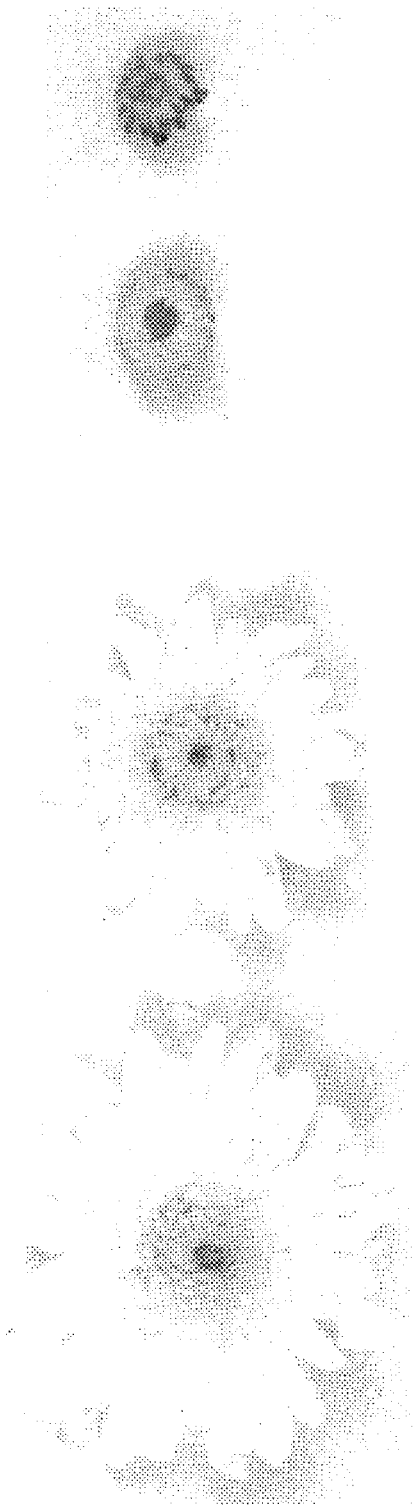
FIG. 2 shows the various stages of bloom of the new cultivar.
Figure 3:
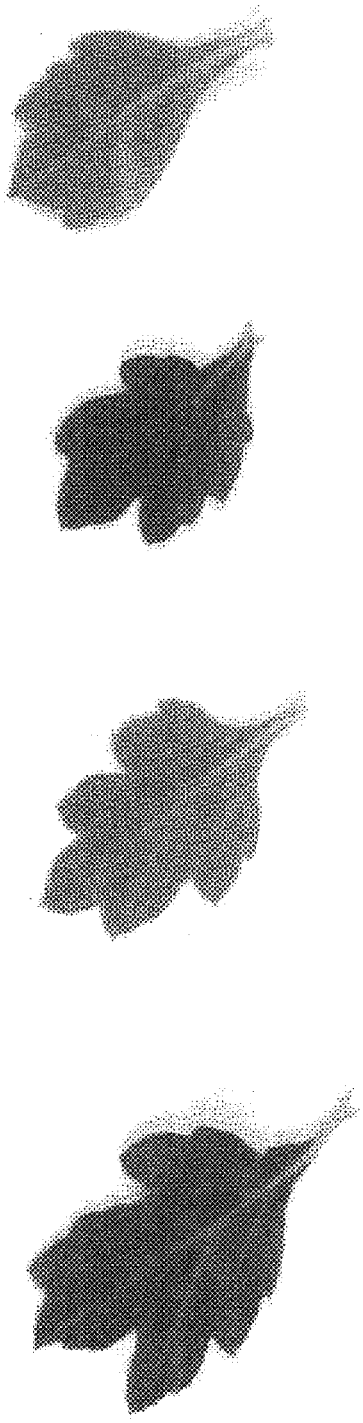
FIG. 3 shows the various stage of foliage of the new cultivar.

The plant shown in the photographic drawings was fifteen (15) weeks old when those photographs were taken.

DESCRIPTION OF THE INVENTION

This new variety of *chrysanthemum* is of the botanical classification *Chrysanthemum morifolium* L. The observations and measurements were gathered from plants grown out door in Rijsenhout, The Netherlands under natural day length and temperature and planted in week 23 in 2005. The natural blooming date of this crop was August 29–September 4 (week 35). The average height of the plants was 25–30 cm cm. The plants were pinched once, just after planting. No growth retardants were used. No tests were done on disease or insect resistance or susceptibility. No tests were done on cold or drought tolerance. This new variety produces medium sized blooms with white ray florets blooming for a period of 5 weeks.

From the cultivars known to inventor the most similar existing cultivar in comparison to Libra is 'Unicorn' (U.S. Plant Pat. No. 14,697). When 'Unicorn' and Libra are being compared the following differences are noticed: The difference of 'Unicorn' and Libra are (1) Flower size and (2) Plant habit. (1) The flowers of 'Unicorn' are smaller in size than those of 'Libra'. (2) The plant form of 'Unicorn' is more erect than the ball-shaped form of plants of 'Libra'.

The following is a description of the plant and characteristics that distinguish Libra as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

| Botanical Description of *chrysanthemum* plant 'Libra' | |
|---|---|
| Bud | |
| Size | Small; cross-section 1 cm, height 0.5 cm |
| Outside Color | Yellow 10D |
| Involucral bracts | 2 rows, length 7 mm, width 3 mm |
| Involucral bracts among disc-florets | Not present |
| Involucral bracts color | Green 138A |
| Bloom | |
| Type | Double |
| Height | 1.5 cm |
| Size | Medium |
| Fully Expanded | 5.5 cm |
| Peduncle length | 9 cm |
| Peduncle color | Green 138B |
| Number of blooms per branch | Approx. 8 blooms per branch |
| Performance on the plant | 5 weeks |
| Seeds | Produced in small quantities, ovate grey-brown 199A, 1½ mm in length. |
| Fragrance | Typical *chrysanthemum,* slightly |
| Color | |
| Center of the flower | Immature Yellow 4A<br>Mature Yellow 4A |
| Color of upper surface of the ray-florets | White 155A |
| Color of the lower surface of the ray-florets | White 155D |
| Tonality from Distance | A garden mum with white flowers and a cream center |
| Color of the ray-florets after aging of the plant | White 155D |
| Ray florets | |
| Texture | Upper and under side smooth |
| Number | 250 |
| Cross-section | Convex |
| Longitudinal axis of majority | Straight to incurving |
| Length of corolla tube | 0.4 cm |
| Ray-floret margin | Entire |
| Ray-floret length | 2-2.5 cm |
| Ray-floret width | 0.5-0.8 cm |
| Ratio length/width | Medium |
| Shape of tip | Rounded |
| Disc florets | |
| Disc diameter | 0.2 cm |
| Distribution of disc florets | Few, only visible in mature stage |
| Shape | Tubular |
| Color | Yellow 4A to Yellow 11D at base |
| Receptacle shape | Conical raised |
| Reproductive Organs | |
| Stamen | Present in disc florets only |
| Stamen color | Yellow-green 144A |
| Pollen | Present |
| Pollen color | Yellow 7A |
| Styles | Thin |
| Style color | Yellow 13A |
| Style Length | 0.3 cm |
| Stigma color | Yellow-green 144A |

TABLE 1-continued

| Botanical Description of *chrysanthemum* plant 'Libra' | |
|---|---|
| Stigma Width | 1 mm |
| Ovaries | Enclosed in calyx |
| Plant | |
| Form | Grown as a spray type potmum, outdoor mounded and round |
| Growth habit | Spherical shape |
| Growth rate | Medium |
| Height | 25-30 cm |
| Width | 45 cm |
| Stem Color | Greyed-brown 199C |
| Stem Strength | Medium |
| Stem Brittleness | Not brittle |
| Stem Anthocyanin Coloration | Absent |
| Internode length | 2 cm |
| Length of lateral branch | From top to bottom 15-20 cm |
| Lateral branch color | Green 138A |
| Lateral branch, attachment | Medium strength |
| Branching (average number of lateral branches) | Good with 7-8 breaks after pinching |
| Natural season blooming date | August 29-September 4 |
| Foliage | |
| Leaf color | Upper side Green 136A-137A<br>Lower side Green 138A |
| Color midvein | Upper side Yellow-green 147D<br>Lower side Yellow-green 148D |
| Size | Small.; length 3-5.5 cm, width 1.8-3.5 cm |
| Quantity (number per lateral branch) | 25 |
| Shape | Elliptic to obovate |
| Texture upper side | Glabrous |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Acute |
| Apex | Mucronulate |
| Petiole length | 1-1.5 cm |
| Petiole color | Yellow-green 147D |

TABLE 2

| Differences with the comparison variety | | |
|---|---|---|
| | 'Libra' | 'Unicorn' |
| Flower size | 5.5 cm | 3.5-4 cm |
| Plant height | 25-30 cm | 28 cm |
| Plant width | 45 cm | 30-34 cm |

I claim:

1. A new and distinct variety of *chrysanthemum* plant as described and illustrated.

* * * * *